(12) United States Patent
Zhu

(10) Patent No.: US 7,449,883 B2
(45) Date of Patent: Nov. 11, 2008

(54) METHOD AND APPARATUS FOR MEASURING CHANGE IN MAGNETIC INDUCTION OF A MAGNETIC MATERIAL WITH RESPECT TO TEMPERATURE

(75) Inventor: Hong Yi Zhu, ShenZhen (CN)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/779,996

(22) Filed: Jul. 19, 2007

(65) Prior Publication Data

US 2008/0018333 A1    Jan. 24, 2008

(30) Foreign Application Priority Data

Jul. 19, 2006    (CN) .................. 2006 1 0088821

(51) Int. Cl.
*G01V 3/00* (2006.01)
(52) U.S. Cl. .................. 324/301; 324/322
(58) Field of Classification Search ......... 324/300–322; 600/407–449
See application file for complete search history.

(56) References Cited

U.S. PATENT DOCUMENTS 6,476,610 B1 * 11/2002 Wiegert et al. .............. 324/345
6,850,804 B2 * 2/2005 Eggers et al. ............... 607/103
7,330,032 B2 * 2/2008 Donnangelo ................ 324/452
7,345,484 B2 * 3/2008 Nakahara et al. ............ 324/322
2004/0014236 A1 * 1/2004 Albo et al. .................. 436/173

FOREIGN PATENT DOCUMENTS

CN    98241658.X    12/1999
JP    98241658.X    12/1999

* cited by examiner

*Primary Examiner*—Brij B Shrivastav
(74) *Attorney, Agent, or Firm*—Schiff Hardin LLP

(57) ABSTRACT

In order to measure the temperature parameters of magnetic materials, in a process and an apparatus for measuring the characteristics of variation of magnetic induction of magnetic material with respect to temperature, a probe is provided at any one point A within the effective imaging range of an MR apparatus, the magnetic material to be tested also being provided at point A. The material is contacted directly with a heating unit, and a temperature sensor is attached to said magnetic material to be tested. The temperature control unit adjusts and controls the heating unit to heat the magnetic material to be tested based on the information collected by the temperature sensor. A processing unit of the MR system controls the probe at A in real-time and receiving the MR signals for feeding into the processing unit of the MR system, and the magnetic induction at A being obtained after the analysis of the system. The temperature parameter of the magnetic material to be tested is calculated by measuring the magnetic induction thereof at A under different temperatures.

12 Claims, 2 Drawing Sheets

METHOD AND APPARATUS FOR MEASURING CHANGE IN MAGNETIC INDUCTION OF A MAGNETIC MATERIAL WITH RESPECT TO TEMPERATURE

BACKGROUND OF THE INVENTION

1. Field of the Invention

The present invention relates to the field of physical science, and in particular the field of magnetic resonance. More specifically, the invention concerns a process and an apparatus for measuring the characteristics of variation of the magnetic induction with respect to temperature.

2. Description of the Prior Art

In the prior art, the pulling process is widely used for determining the temperature parameter of a magnetic material, i.e. pulling a test coil at pre-set temperature. While the test sample is placed inside a silica tube in the test coil, the magnetic characteristic of the sample under this temperature is obtained and recorded through the process of pulling the test coil. A disadvantage of this measuring apparatus is that the pulling of the test coil has to be done identically each time, because the measurement precision of each sample is determined by the manual pulling speed of the operator. If the error of the pulling speed is relatively large, then the measurement precision will deviate notably, leading to the insurmountable disadvantage of huge manual operating errors of this apparatus. Furthermore, this measuring apparatus can test only one sample magnetic material each time (due to the limitations of manual pulling), thus using this measuring apparatus in the testing procedure results in problematic waste in time, money and energy. In addition, this measuring apparatus also has shortcomings like fragility and low reproducibility of the measurement results each time, etc.

Chinese Utility Model application No. 98241658.X, filed on Oct. 22, 1998 and entitled "Measuring Apparatus of the Temperature Parameter of Permanent Magnets", discloses an apparatus with a heating furnace on a platform inside the magnet shielding mask. The sample chamber and the sample material are disposed in the furnace, while the furnace is enclosed by a cooling jacket and covered with an insulation cover. A probe and its support are fixed on the platform. The probe, the magnetometer and the drawing instrument are connected in series, with the thermocouple being connected to the drawing instrument. However, this apparatus has a relatively complicated structure, and a special apparatus is needed to measure the temperature parameter of the magnet sample and hence the cost is relatively high.

Magnetic materials like amorphous alloys are commonly used to achieve the homogeneous background magnetic field in current MRI (magnetic resonance imaging) systems. The providers of magnetic materials (e.g. amorphous alloys) seldom provide the temperature parameters of their product. To design the magnet of the MRI system and estimate its stability, it is important to obtain the temperature parameters of relevant magnetic materials.

For some manufacturers who make MRI systems, it is essential to obtain the temperature parameters of the permanent magnetic or ferromagnetic materials in their products. However, purchasing new equipments for obtaining the temperature parameter will increase the cost, and the measuring result is not very accurate.

SUMMARY OF THE INVENTION

An object of the present invention is to provide a process and an apparatus for measuring the characteristics of variation of magnetic induction of magnetic materials with respect to temperature wherein the aforementioned problems are avoided or minimized, and to measure the temperature parameter of magnetic materials precisely with existing MRI systems.

This object is achieved in accordance with the invention by a process for measuring the characteristics of variation of magnetic induction of the magnetic material with respect to the temperature, includes:

a probe provided at any one point A within the effective range of the magnetic field of an MR system, measuring the MR signal of this point and the processing unit of the MR system calculating the background magnetic induction $B_0$ at the point;

providing a magnetic material to be tested at the point A, the temperature control unit of the MR system controlling a heating unit to heat the magnetic material to be tested, detecting the temperature of the magnetic material with a temperature sensor, measuring the MR information with the probe, and the processing unit of the MR system, based on the information, calculating the corresponding magnetic induction of the magnetic material at the point A with respect to different temperatures;

subtracting said background magnetic induction $B_0$ from each said magnetic induction, obtaining the magnetic induction of the magnetic material itself under each of these temperatures, and obtaining the characteristics of variation of magnetic induction of the magnetic material to be tested with respect to the temperature.

The probe is formed by a transmitter-receiver coil and a sample detecting sphere disposed in the coil. The transmitter-receiver coil sends radio frequency pulse sequences to the detecting sphere to activate the detecting sphere to generate MR signal, and receives the MR signal and feeds it back into the processing unit of the MR system, which calculates the magnetic induction at the location of the detecting sphere.

The sample detecting sphere contains hydrogen or carbon.

The step of the temperature control unit of said MR system controlling said heating unit and said temperature sensor can include, with the temperature control unit, controlling the heating unit to heat the magnetic material to be tested at rated power if the present temperature of the magnetic material to be tested detected by said temperature sensor is lower than a pre-set temperature. The temperature control unit controls said heating unit to heat the magnetic material to be tested at a pre-set power lower than the rated power if the present temperature of the magnetic material to be tested detected by the temperature sensor is higher than the pre-set temperature.

The heating unit can use thermal conduction, thermal radiation or a combination of both to heat the magnetic material to be tested.

An apparatus in accordance with the invention for measuring the characteristics of variation of magnetic induction of magnetic material with respect to temperature, includes:

the magnetic material to be tested, disposed within the effective range of the magnetic field of the MR system;

a temperature sensor for detecting the temperature of the magnetic material to be tested;

a heating unit for heating the magnetic material to be tested;

a temperature control unit for receiving signals from the temperature sensor and controlling the heating unit to heat the magnetic material to be tested;

a probe for detecting the magnetic induction at a certain point within the effective range of the magnetic field;

a processing unit of the MR system for receiving the MR signal measured by the probe and calculating the magnetic induction information at the point.

The probe can be formed by a transmitter-receiver coil and a sample detecting sphere disposed in the coil and the transmitter-receiver coil sends radio frequency pulse sequences to the detecting sphere to activate the detecting sphere to generate MR signal. The transmitter-receiver coil receives said MR signal and feeds it back into the processing unit of the MR system, which calculates the magnetic induction at the location of the detecting sphere.

The detecting sphere contains hydrogen or carbon.

The temperature control unit refers to the temperature control unit of the MR system or a temperature control unit separated from the MR system.

The magnetic material to be tested is disposed above the heating unit, and the probe is disposed above the magnetic material to be tested.

A fixed device is also included, for supporting the heating unit and the magnetic material to be tested.

The temperature sensor is in direct contact with the unknown magnetic material.

An advantage of the present invention is that it is possible to measure the temperature parameter of magnetic material using existing MRI system with less cost and higher precision.

DESCRIPTION OF THE PREFERRED EMBODIMENTS

In the following, the present invention will be described in detail in combination with the accompanying figures.

Figure 1:
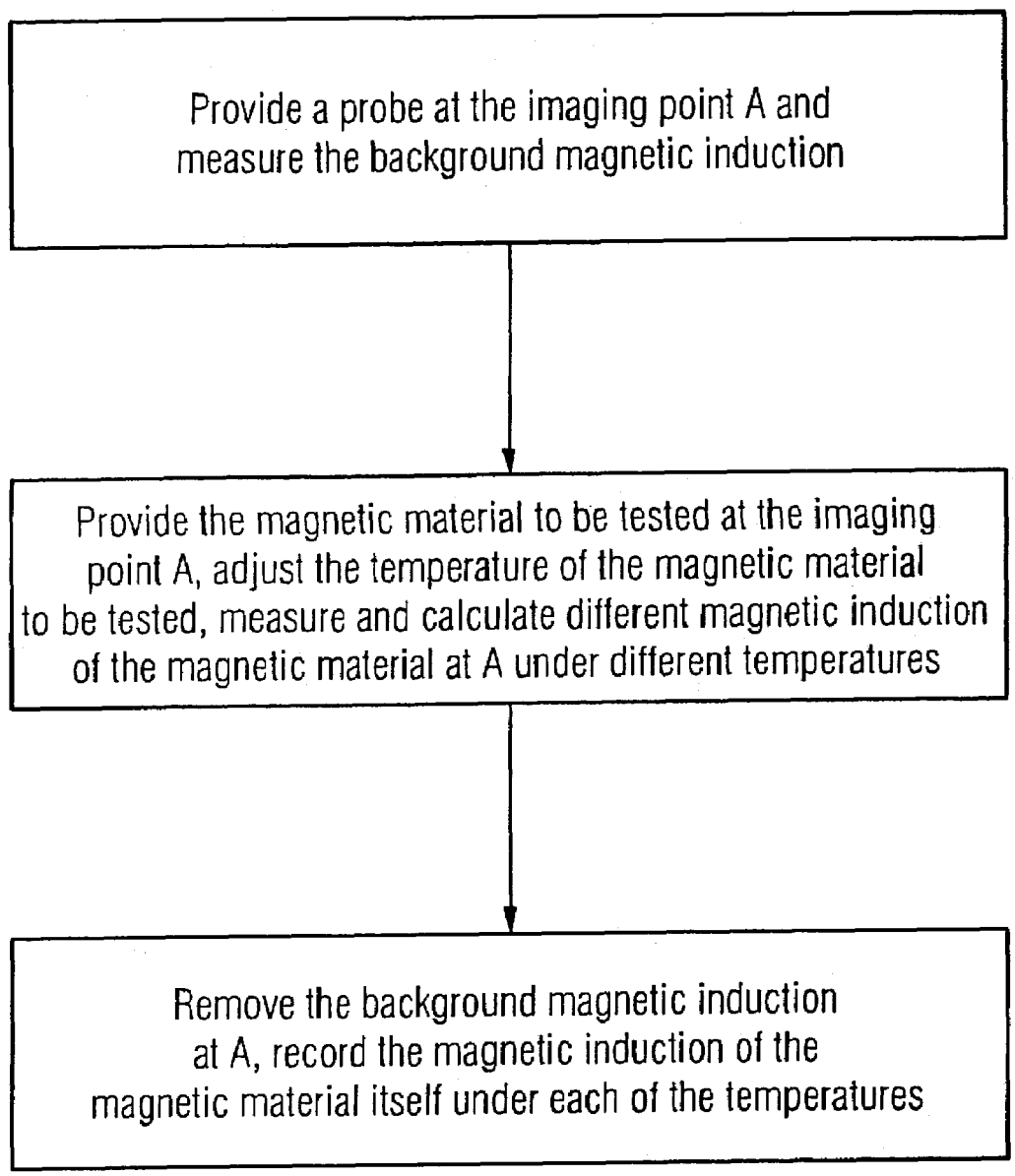
FIG. 1 is a flowchart of the present invention.

A flowchart of the present invention is shown in FIG. 1.

A probe is provided at any one point A within the effective range of the magnetic field of the MR apparatus. It measures the MR signals of this point, and the background magnetic induction $B_0$ is calculated by the processing unit of the MR system;

The probe is a coil g with a small hydrogen-containing sphere f in the center thereof. Since the MRI system optimizes the resonance signal for human tissues, the small sphere f is preferably made of silica gel which is similar to the human tissues. Alternatively, carbonaceous materials can be used for making the detecting sphere and the MR signal at the sphere can be obtained by utilization of the characteristics of carbon measurement of the MR system. The probe is connected into the MR system, and the processing unit of the MR system controls the coil g to send radio frequency pulse. The coil g is a common transmitter-receiver coil in the existing MRI system. The pulse activates the silica gel sphere f to generate an MR signal, and the coil g receives the signal and sends it to the MR system, which analyzes and obtains the resonant frequency $f_0$, and calculates the magnetic induction $B_0$ of the present background magnetic field at point A through $B_0 = 2\pi f_0/\gamma$ ($\gamma$ is the magnetogyric ratio of hydrogen, $\gamma = 2.68 \times 10^8$ rad/(s*T), wherein rad stands for radian, s stands for second, and T stands for tesla).

Magnetic material to be tested is provided at said point A. The temperature control unit of the MR system controls a heating unit to heat the magnetic material to be tested. A temperature sensor collects the temperature of the magnetic material and the probe measures the MR information. The processing unit of the MR system, based on this information, calculates the corresponding magnetic induction of the magnetic material to be tested at A under different temperatures.

The magnetic material to be tested, the heating unit and a non-magnetic weight (the base) are fixed together. The heating unit is disposed in intimate contact with the magnetic material to be tested and heats the material through thermal conduction. Alternatively, the heating unit can be connected with the space in which the magnetic material to be tested is disposed and heats the material through thermal radiation. The temperature sensor is fixed on the magnetic material to be tested, and the heating unit and the temperature sensor are respectively connected to the power output and the temperature collection terminal of the temperature control unit of the MR system. The magnetic material to be tested, the heating unit and the non-magnetic weight are disposed at point A within the MRI area, such that the magnetic material to be tested is disposed as close to point A as possible. If no terminal of the temperature control unit of the MR system is available, an additional temperature control unit can be used, which connects with the heating unit and the temperature sensor, and adjusts the heating current output through some algorithm such as proportional integral differential (PID) control, and thus controls the temperature of the heating unit.

The temperature control unit controls said heating unit to heat the magnetic material to be tested to a pre-set temperature $T_1$;

The MR signal of the magnetic material to be test at A under $T_1$ is measured and the magnetic induction $B_1$ at this point is calculated;

The magnetic material to be tested is heated to $T_2$;

The MR signal of the magnetic material to be tested at A under $T_2$ is measured and the magnetic induction $B_2$ at this point is calculated;

The magnetic material to be tested is heated to $T_3, T_4, \ldots T_n$, and the corresponding MR signal of the magnetic material at A under $T_3, T_4, \ldots T_n$, are respectively measured and the magnetic induction $B_3, B_4, \ldots B_n$ are calculated.

Background magnetic induction $B_0$ is subtracted from each measurement of the magnetic induction, to obtain the magnetic induction of the magnetic material itself under each of these temperatures (excluding the magnetic induction of the background magnetic field), and thus the characteristics of variation of magnetic induction of the magnetic material to be tested with respect to the temperature is obtained.

A curve of the temperature T and the magnetic induction B at A is drawn. The characteristics of the ferromagnetic material in the background magnetic field $B_0$ with respect to the variation of the temperature can be obtained, since A is very close to the magnetic material to be tested.

Of course, the magnetic induction of the magnetic material to be tested under different temperatures can be measured first, then the material is taken away from the effective magnetic field of the MRI, and the background magnetic induction is measured. Subsequently, the magnetic induction of the magnetic material itself is calculated, and the characteristic curve of the magnetic material to be tested with respect to the variation of temperature can be obtained.

Figure 2:
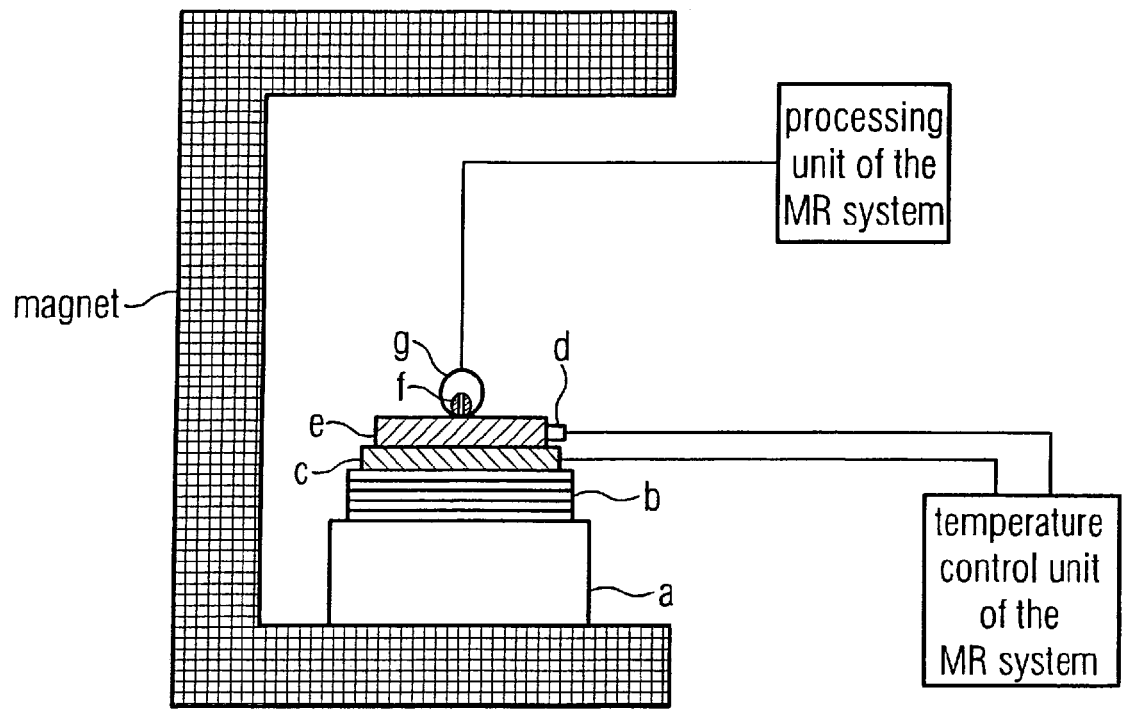
FIG. 2 is a schematic diagram of the apparatus according to the present invention.

A schematic diagram of the apparatus according to the present invention is shown in FIG. 2. In the present MRI system, a fixing device b is provided directly below point A within the effective imaging range of MRI. The fixing device is provided on a hospital-bed a for fixing the magnetic material e to be tested. In this example, the magnetic material e is ferromagnetic. A heating unit c is provided on the fixing device. The heating unit preferably uses simple-structured metal pieces to heat the ferromagnetic material to be tested or to maintain the temperature. Non-magnetic metal materials like aluminum can be chosen for the metal piece, in order to reduce the interference of the magnetic field and increase the measurement precision of the temperature parameter. The heating unit can be either in intimate contact with or kept a certain distance from the ferromagnetic material to be tested. The way in which they are in contact is not limited herein. The heating unit can be either clung to the material to be tested on upper or lower side. The material to be tested can also be placed inside the heating unit, with the heating unit heating the material to be tested while half-enclosing it. It is also possible to heat the magnetic material to be tested through heat radiation, with the main purpose of minimizing the loss of heat and the falling of temperature. Being in direct contact with the unknown ferromagnetic material, temperature sensor d is used for returning the temperature of the material to be tested in real-time.

Figure 3:
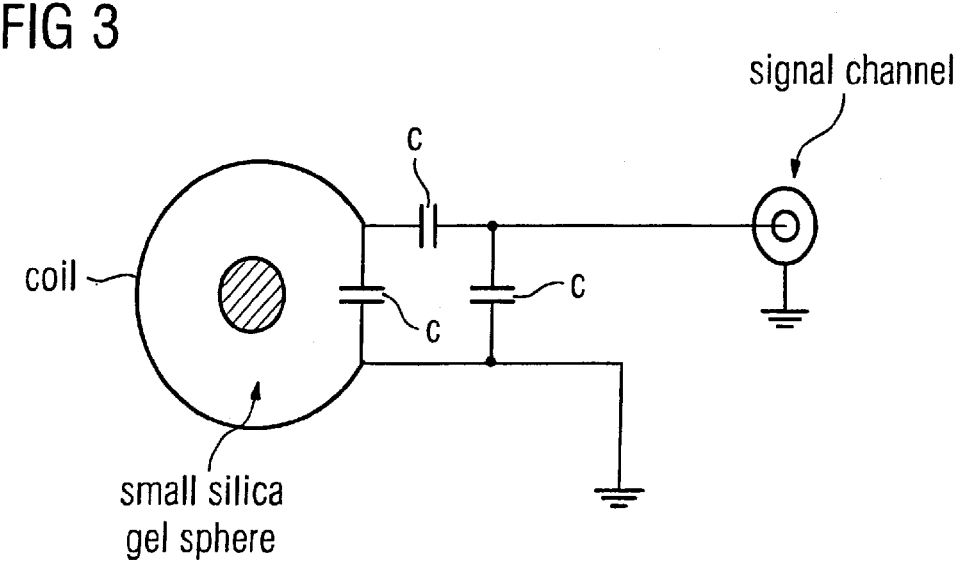
FIG. 3 is a schematic diagram of an embodiment of the probe according to this invention.

Connected with the temperature sensor d and the heating unit c, the temperature control unit is used for receiving the temperature measurement information from the temperature sensor d and controlling the heating unit c in its heating process. Both the temperature control unit in the present MRI system and additional temperature control unit separated from the MRI system can be adopted for the temperature control unit. The probe consists of a transmitter-receiver coil g and a small silica gel sphere f (as is shown in FIG. 3) in the coil. The transmitter-receiver coil is connected with the local coil terminal of the MRI system, while the small silica gel sphere f is enclosed by the coil at the center of the coil. Activated by the RF signals sent by the coil, the small silica gel sphere generates MR signals.

This signal is then received by the coil and sent to the MR system for analysis. The resonant frequency of the small sphere can be calculated. The average magnetic induction B within the range of the small silica gel sphere can be calculated based on this frequency. The probe is in contact with the measurement point of the magnetic material to be tested, and therefore calculating the magnetic induction B of the probe means obtaining the magnetic induction of the magnetic material to be tested. Since many magnetic materials, when activated in a magnetic field, would generate a magnetic field that is not homogeneous enough, it can seldom be measured precisely by the common magnetic induction measuring devices, such as a gauss meter. Since the probe of a gauss meter is relatively large in size it cannot carry out a precise measurement of the magnetic induction at a certain point in the magnetic field. The probe in the present invention, however, can be made quite small, and thus the homogeneity of the magnetic field within the coverage of the probe can be relatively better. Thus it is possible to carry out a precise measurement for a certain point in the magnetic field.

An apparatus in the present MR system used for measuring the magnetic field is called a shim array, which has a number of probes distributed on one circular arc or hemi-circular arc, for simultaneously measuring the magnetic field at a plurality of points, mainly used for the debugging of the homogeneous magnetic field in the MR systems. Only one probe is necessary in the present invention. It is possible to directly embody a probe in the shim coil, or make a smaller coil modeled on the shim coil. Since the obtained magnetic induction is the average value within the space of the small silica gel sphere, "point measurement" can be realized when the small sphere is small enough. The processing unit of the MR system is used for controlling the RF pulse and signal collection (transmitting & receiving). Since a MR system is directly used herein, it is only necessary to connect the probe (a coil enclosing a silica gel sphere) with the terminal once used for connecting the local coil of the MR system, and then the system can operate.

All the above magnetic material to be tested, heating unit, temperature sensor and probe can be either single or multiple. The temperature parameters of multiple magnets can be measured at the same time.

The temperature sensor is attached to the magnetic material to be tested, with the output line of the sensor being connected to the temperature control unit of the MR system. The temperature control unit calculates appropriate output voltage and current according to the present temperature measured by the temperature sensor, and output it to the heating unit. Preferably, the temperature control unit carries out the following steps: it calculates the most appropriate current and output it to the heating unit, according to the present temperature of the magnetic material to be tested measured by the temperature sensor and a pre-set temperature. For example, if the present temperature has not yet reached the pre-set temperature (e.g. 10° C.), the output will be at rated power for heating; if the present temperature of the sample is already higher than the pre-set temperature (e.g. 10° C.), then the output power needs to be reduced, e.g. to 10% of the rated power, to prevent overshooting (the temperature exceeds the target temperature excessively). When the temperature is stabilized under target temperature, it is necessary to change the output current dynamically and instantaneously, in order to even the heat gained from the heating unit and the heat lost due to the difference of environment temperature, thus the temperature of the sample can be maintained stabilized under target temperature.

There are temperature control units in every permanent magnetic resonance system, mainly for controlling the temperature of the system during its operation process, because the magnet will be affected if the temperature excesses the specified value. To directly control the temperature, it is only necessary to add an additional temperature sensor and a heating unit to the magnet material to be tested and connect the other end to the temperature control unit of the MR system. If the output channels of the temperature control unit of the MR system are all occupied, a same external temperature control unit can be connected externally, to control the temperature of the magnetic material to be tested and measure the relation between the temperature of the magnetic material and the magnetic induction.

An advantage of the present invention is that the temperature parameter of ferromagnetic materials can be conveniently and precisely obtained using the MRI system, and the present invention provides an additional application for the MRI system. Furthermore, the present invention and its apparatus are simple in structure and less expensive in cost.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A method for measuring variation of magnetic induction of a magnetic material with respect to temperature, comprising the steps of:

in a magnetic resonance system that generates a magnetic field, providing a probe at an arbitrary point A within an effective range of said magnetic field and measuring magnetic resonance signals at said point A, and from the measured magnetic resonance signals automatically electronically calculating a background magnetic induction $B_0$;

providing a magnetic material to be tested at said point A, and operating a temperature control unit of the magnetic resonance system to control heating of said magnetic material to be tested, and detecting a temperature of said magnetic material with a temperature sensor while measuring magnetic resonance signals with said probe, and automatically electronically calculating, from said temperature and said magnetic resonance signals, a magnetic induction of said magnetic material at said point A at respectively different temperatures; and for each measurement of magnetic induction at each of said respectively different temperatures, subtracting said background magnetic induction $B_0$ from the magnetic induction measured for said magnetic material to obtain a plurality of subtraction results, and combining said subtraction results to obtain a characteristic curve representing variation of the magnetic induction fo the magnetic material with respect to temperature.

2. A method as claimed in claim 1 comprising employing, as said probe, a transmitter-receiver coil and a sampled detecting sphere disposed in said coil, and emitting radio frequency pulse sequences into said detecting sphere to activate said detecting sphere to generate said magnetic resonance signals, and receiving said magnetic resonance signals with said coil and supplying said magnetic resonance signals to a processing unit, and automatically calculating said background magnetic induction $B_0$ and said magnetic induction of said magnetic material being tested in said processing unit.

3. A method as claimed in claim 2 comprising, as said sample detecting sphere, using a sample-detecting sphere containing an element selected from the group consisting of hydrogen and carbon.

4. A method as claimed in claim 1 comprising using a heating unit of said magnetic resonance system to heat said magnetic material to be test, and comprising controlling said heating unit to heat said magnetic material to a reference power if the temperature of said magnetic material detected by said temperature sensor is lower than a predetermined temperature, and controlling said heating unit to heat said magnetic material to said predetermined power, that is lower than said reference power, if said temperature of said magnetic material detected by said temperature sensor is higher than said predetermined temperature.

5. A method as claimed in claim 1 comprising heating said magnetic material with a heating unit selected from the group consisting of thermal conduction heating units, thermal radiation heating units, and combined thermal conductive/thermal radiation heating units.

6. An apparatus for measuring changes in magnetic induction of a magnetic material with respect to temperature, for use in a magnetic resonance system that generates a magnetic field comprising:

a temperature sensor that detects a temperature of a magnetic material to be tested located within an effective range of said magnetic field of said magnetic resonance system;

a heating unit that interacts with said magnetic material to heat said magnetic material while detecting said temperature;

a temperature control unit that receives signals from the temperature sensor and that controls said heating unit to maintain said magnetic material at a controlled temperature dependent on the temperature detected by said temperature sensor;

a probe that interacts with said magnetic material to detect magnetic resonance signals from said magnetic material in said effective range of said magnetic field; and a processing unit of the magnetic resonance system that receives said magnetic resonance signals and the temperature detected by said temperature sensor, and that calculates a magnetic induction of the magnetic material at said point and at each temperature.

7. An apparatus as claimed in claim 6 wherein said probe comprises a transmitter-receiver coil and a sample detecting sphere disposed in said coil, said transmitter/receiving coil emitting radio frequency pulse sequences into said detecting sphere to activate said detecting sphere to generate said magnetic resonance signals, and said transmitter-receiver coil receiving said magnetic resonance signals and supplying said magnetic resonance signals to said processing unit.

8. An apparatus as claimed in claim 7 wherein said detecting sphere contains an element selected from the group consisting of hydrogen and carbon.

9. An apparatus as claimed in claim 6 wherein said temperature control unit comprises a temperature control unit of said magnetic resonance system.

10. An apparatus as claimed in claim 6 comprising a fixture that holds said magnetic material during testing thereof above said heating unit, and wherein said probe is disposed in said fixture above said magnetic material.

11. An apparatus as claimed 6 comprising a fixture that maintains said temperature sensor in direct contact with said magnetic material.

12. An apparatus as claimed 6 wherein said heating unit is a heating unit selected from the group consisting of thermally conducting heating units, thermally conducting heating units, thermally radiating heating units, and combination thermally conductive/thermally radiating heating units.

* * * * *